Figure 1:
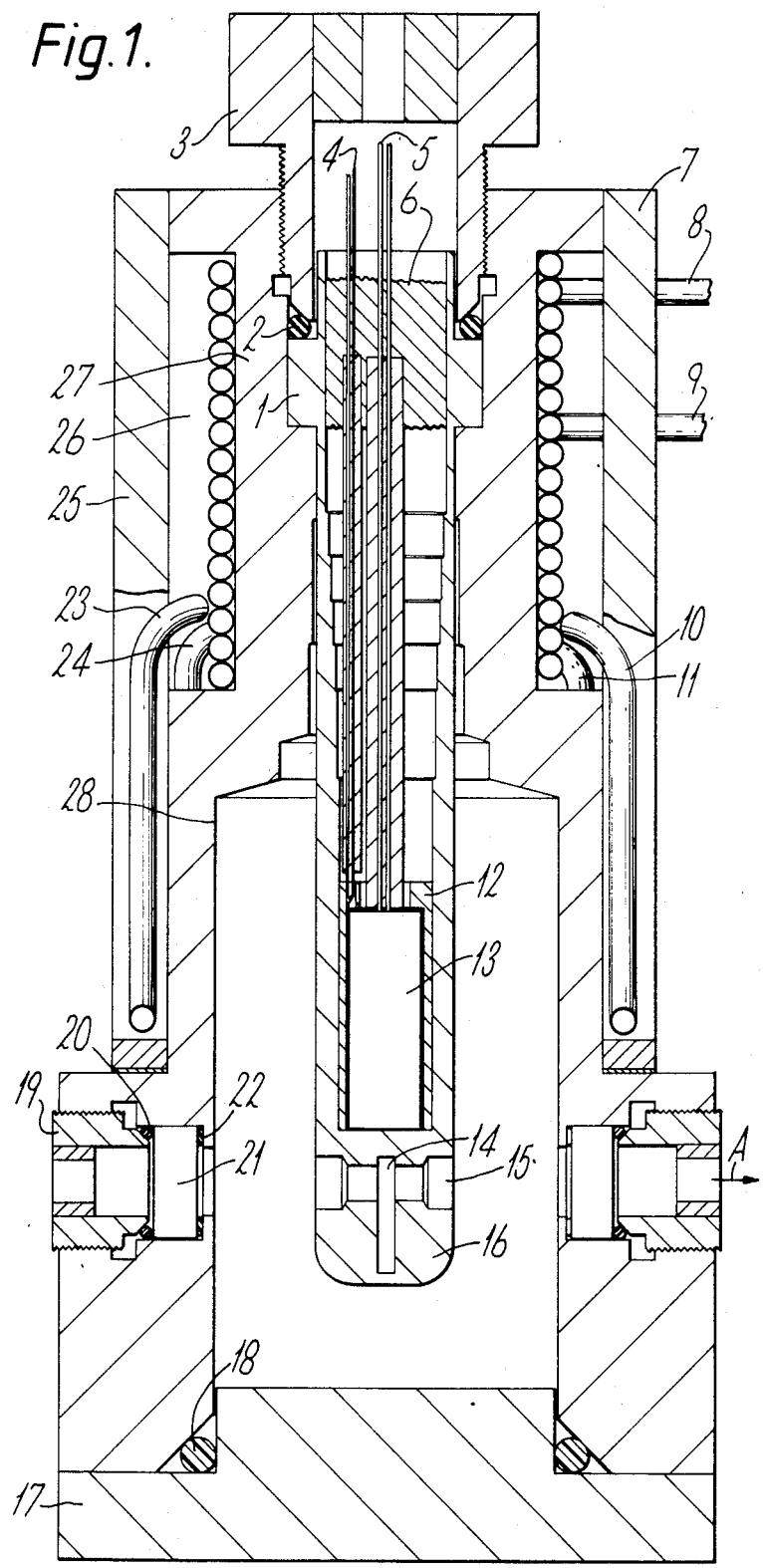

United States Patent [19]

Rossiter

[11] Patent Number: 4,674,876
[45] Date of Patent: Jun. 23, 1987

[54] MULTI-MODE CELL FOR SPECTROSCOPY

[76] Inventor: Valentine J. Rossiter, 16 Rathmore Avenue, Stillorgan Co. Dublin, Ireland

[21] Appl. No.: 704,683

[22] Filed: Feb. 22, 1985

[30] Foreign Application Priority Data

Feb. 22, 1984 [GB] United Kingdom ................ 8404704

[51] Int. Cl.⁴ .......................................... G01N 21/01
[52] U.S. Cl. .................................................. 356/244
[58] Field of Search ................. 356/244; 250/428, 429

[56] References Cited

U.S. PATENT DOCUMENTS 3,869,215 3/1975 Nolan .................................. 250/429
4,158,772 6/1979 Reedy ................................. 356/244

FOREIGN PATENT DOCUMENTS 1207160 9/1970 United Kingdom ................ 356/244

OTHER PUBLICATIONS

Andereev et al., "Universal Cryostat Attachment for the SF-4A Spectrophotometer" in Strum-Exp. Tech. (U.S.A.), vol. 21, #6, Nov.-Dec. 1978 (Pub. Jun. 1979), pp. 1658-1659.
Krauss et al., "Temperature Regulating Device for Infrared Spectroscopy" Monthly Technical Review, vol. 15, #8, Aug. 1971, pp. 159-160.

Primary Examiner—Vincent P. McGraw
Attorney, Agent, or Firm—Sughrue, Mion, Zinn, Macpeak, and Seas

[57] ABSTRACT

A cell for spectroscopy allow examination of a sample under wide ranges of temperature and pressure conditions and by different modes of operation. A sample to be examined is housed at the end of a probe (1) which projects into and is enclosed within a housing. Heating and/or refrigerating means can act on the sample, which may be mounted so that radiation emitted through a window in the housing emanates from the part of the sample nearest the heating or refrigerating means. The probe has a wall of a thickness which diminishes along its length away from the end and the housing has a wall of a thickness which increases in the same direction. An end cap of the housing is removable and replaceable by other end caps having e.g. mirrors to enable reflection spectroscopy or further refrigerating means.

19 Claims, 4 Drawing Figures

MULTI-MODE CELL FOR SPECTROSCOPY

There is a requirement for a device suitable to facilitate the examination of the behaviour of materials under various combinations of extreme physical conditions of temperature and pressure by means of spectroscopy. To meet these requirements, it is necessary to provide a means of varying the temperature of samples between low and high values (say from $-200°$ C. to $+700°$ C.) and varying the composition and pressure of the surrounding atmosphere for the sample from high vacuum to high pressure (say from one nano-torr to 5000 psig); throughout these changes the sample may usefully be exposed to reactive or inert gases or may be in contact with other materials with which it may undergo physical or chemical changes. It is also advantageous if the sample can be examined spectroscopically in essentially the same device in modes other than transmission, as samples of interest may not be in a form where significant amounts of radiation are transmitted. The invention described here meets all these requirements in a single device which is sufficiently small that, for example, in one form it fits the sample compartment of standard commercial infrared spectrophotometers.

We achieve these aims according to the invention by providing an outer housing, through which access and egress for examining light is available and a probe within the housing, one end portion of the probe being spaced from the housing, this end portion of the probe having means for mounting a sample to be spectrosocopically examined, the said end portion of the probe being maintainable at a temperature substantially independent of that of the housing.

The probe will usually be metallic with a comparatively massive said one end portion, a second end portion of the probe being mounted in the housing. Heating and/or refrigerating means are associated with the first mentioned end portion whereby desired temperature conditions are obtained at that portion. This portion may include a holder for a sample to be examined which is arranged such that the portion of the sample interacting with the examining light is most closely adjacent to the heating and/or refrigerating means. The holder may be such as to fit a standard sample cell into it; but in this case since the sample cells are broad the examining light will preferably impinge off-centre of the cell, nearer an edge which is most adjacent to the heating/refrigerating means.

When the probe is of metal, the vary substantial heating to which its said one end portion may be subjected may cause weakening of the metal (which also may be subjected to substantial pressure changes within the housing). However, the other end portion of the probe which is mounted in the housing will not be subjected to the same temperature pressure range and both for economy of manufacture and to assist in sharpening the temperature gradient along the probe between its ends, the probe is preferably formed with progressively decreasing wall thicknesses as one moves from the first mentioned end portion to the second mentioned end portion. Similarly, the walls of the housing may diverge away from the probe in the direction in which one moves from the second mentioned end of the probe to the first mentioned end.

The mounting of the probe on the housing may be achieved at one end portion of an essentially cylindrical housing at which the housing and probe are in direct contact, and its other end, which is spaced from the first mentioned end portion of the probe, may be formed with a removable end closure. This end closure may be a plain closure, or be replaceable by, an end closure allowing a desired form of examination and/or of temperature control to be carried out in the probe. For example, an alternative end closure to the housing might allow for ingress and egress of refrigerating fluid for the end of the probe and another, still fittable into the same housing, be provided with inclined reflecting surfaces whereby specular examinations of a sample held in the probe may be carried out. A more normal conformation will use optical access and egress points which are aligned across the housing and through the one end portion of the probe.

The housing may be provided, adjacent the position of mounting of the probe to it, with auxiliary temperature-control means.

The invention is illustrated with the aid of FIGS. 1, 2, 3 and 4 which are diametric at cross-sections through respective embodiments.

Referring to FIG. 1, this shows a general cross-section where a probe 1 is a cylindrical tube normally arranged to lie in the horizontal plane in a housing 27. One end portion 16 of the probe is to hold the sample in a cavity 14 open to one face of the tube and which radiation may pass by means of an aperture 15. This end portion 16 is spaced from all parts of the housing 27. The probe 1 contains a heater 13 inserted in a sleeve 12. This sleeve 12 in turn accommodates a thermocouple or other temperature sensing device 4. The cylindrical sleeve 12 is a very close fit to the cylindrical heater 13 and the sleeve 12 is a sliding fit in its location within the probe 1. The cavity 14 is centred off the optical axis through the aperture so that it can conveniently accommodate samples of (say) the standard 13 mm diameter while still ensuring that area of the sample undergoing spectroscopic examination is in a region of very uniform temperature nearest to the heater. The temperature sensing leads 4 and the heater power leads 5 which, it is to be noted, are not within the experimental region, are electrically insulated with high temperature material (typically ceramic) as they emerge from the sleeve 12 until they reach a plug 6 which is a silicone rubber plug encapsulating the electrical leads as they emerge from the probe 1; conventional electrical insulation may be used on leads 4 and 5 after they pass through the plug 6. Note that the internal diameter of the tube 1 increases between the location of the heater 13 and the silicone rubber plug 6 and that this alteration in internal diameter commences outside the region designed for very high temperature and proceeds in a series of small increments. This is part of the means used to induce a temperature gradient from the end 16 of tube 1 to its other end position and in particular to the region occupied by plug 6 and to reduce heat transfer between these locations through the probe 1. The increased wall thickness of the probe 1 in the region 16 liable to be exposed to maximum temperature allows it to withstand the effects of high pressure at such temperatures. Note also that probe 1 is in surface to surface contact with the housing 27 only in the region of the plug 6 and also that the inner surface 28 of the housing 27 is brought progressively closer to the probe 1 before they make contact. This also aids the sharpening of the temperature gradient along probe 1. The temperature of the housing 27 in the region of contact is controlled by fluid circulating through tubes 8 and 9 which are coiled around the housing 27 and which may also be led to other regions of the cell body as illustrated by tubes 10, 11, 23, 24. The outer temperature of the cell is further controlled by containing these coils of tubing with plates 7, 25 and 26 which are three of the four used to jacket the inner surface of the housing. This temperature controlled region ensures that the temperature of the cell body 27 is regulated so as to be acceptably near a chosen temperature, e.g. ambient temperature, when the cell is used to heat samples or to cool samples (see below).

The housing 27 is designed to take means for ingress and egress of light for examining the samples, e.g. two sealed window systems (alternative window systems could also be provied for other modes, for example for Raman Spectroscopy), one of which consists of a threaded ring 19 with an axial aperture to transmit the radiation and which can be tightened by a hexagonal spanner to bear down on the O-ring 20 with an appropriately angled contact face. This O-ring 20 in turn seals against the body of the housing 27 and the window 21. A thin gasket 22 for example of Teflon (Trade Mark) is provided between the window 21 and the housing 27. This window arrangement is efficient, compact, pressure and vacuum tight, and demountable.

The housing 27 also has an end-plate 17 similarly sealed by using three screws to clamp it on in such a way that an O-ring 18 forms a gas tight seal.

A final pressure seal is on the probe 1 which is sealed as it exits from the cell body 27 by an O-ring 2 compressed by means of a hollow threaded bolt 3 which has an appropriately angled contact face. Access can be gained to the sample cavity 14 by removing either the probe 1 or the end plate 17. It will be noted that these demonstrable elements are in low-temperature regions so that screw-threaded parts may be used for these purposes.

The arrangemnt shown in FIG. 1 is suitable for obtaining either the transmission or emission spectra . of samples and can be readily extended to provide Raman Spectra. The entire housing shown in FIG. 1 is rigidly mounted on a base plate whose height, tilt and lateral position with respect to the optic axis can be varied by adjusting a screw system which locates the mounting plate on a fixed support bracket. A system of pipes can be fabricated in the housing 27 to allow the entrance of gases under pressure, or to evacuate the cell chamber, or to allow the admission of other probes into the experimental region. Using modern machining methods, these pipes can be fabricated from the original block from which the housing 27 is manufactured, so avoiding welds or other joins within the structure; these pipes are not illustrated in FIG. 1. All the materials may be chosen to be extremely inert so that sample materials do not undergo corrosive or other undesirable reactions with the probe or housing. Stainless steels may, for example, be used.

Figure 2:
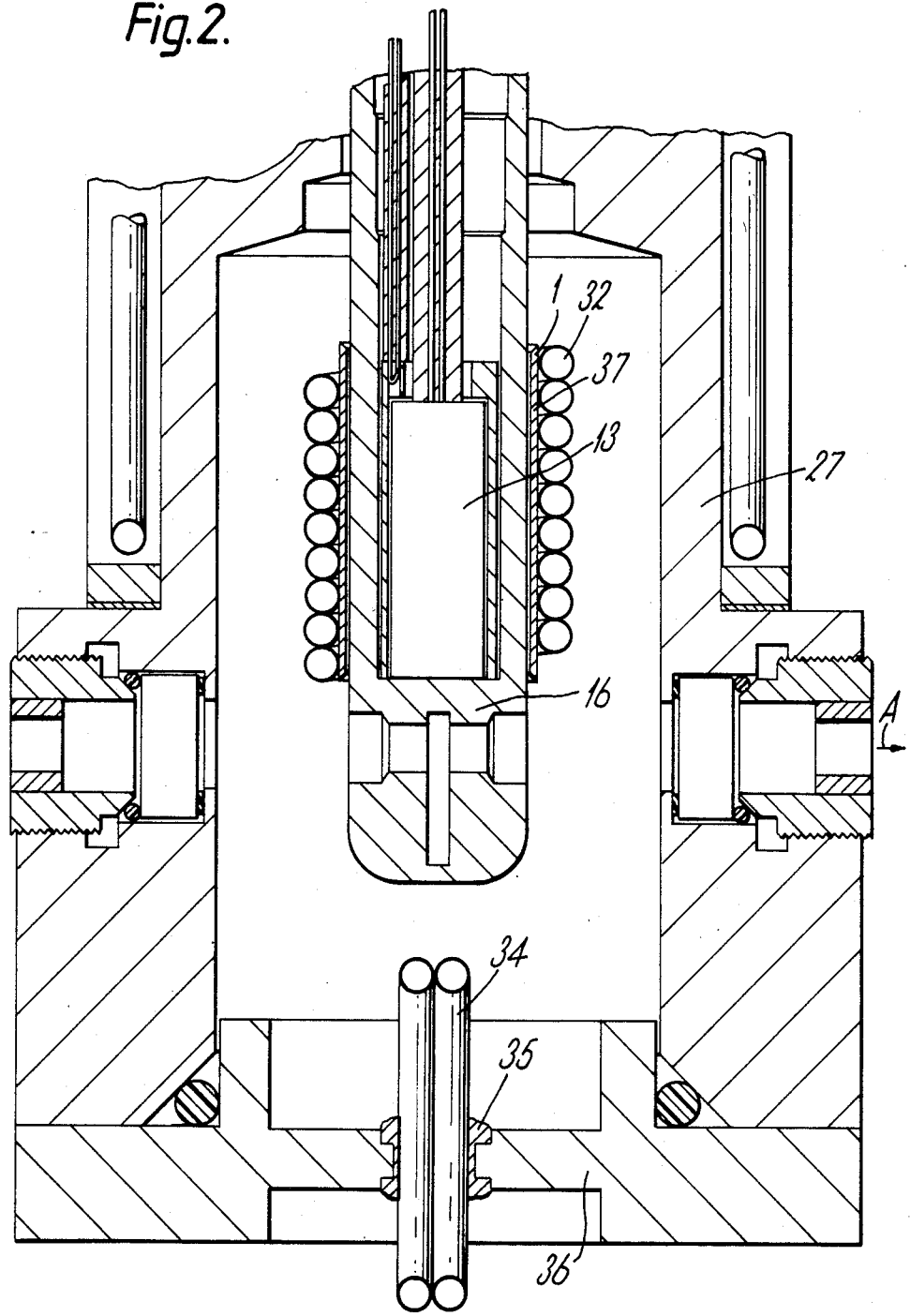

FIG. 2 illustrates a method of achieving low temperatures within the housing, and in particular at the end portion 16 of the probe 1. The method utilises a cold fluid circulating through a coil of tubing introduced through an alternative demountable end plate 36. The end plate 36 is cut away in the region of the coil entrance/exit 34 to avoid undesirable thermal transfer and is suitably sealed by packing 35 as the cooling tubes pass through it. The cooling is effected by means of a sleeve 37 which is bonded to a coiled portion 32 of the tube 34 located in the region close to the location of the heating element 13. Temperatures of at least as low as −200° C. can be achieved by such means in the end portion 16; lower temperatures could be achieved by using colder fluids. Other features are as illustrated in FIG. 1 and described above; the cell can reach high temperatures even with the cooling system installed and can also operate under pressure or vacuum.

Figure 3:
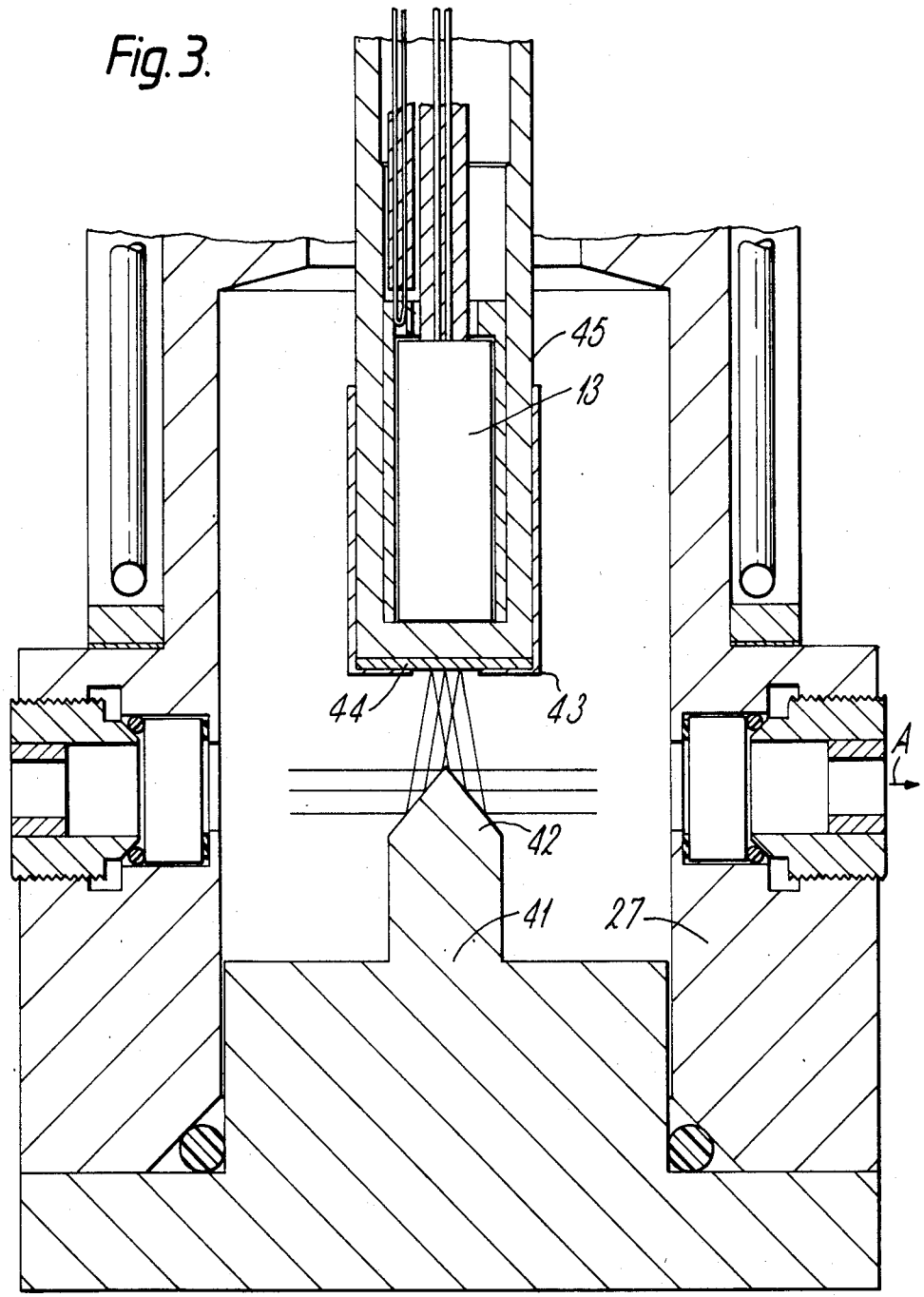

FIG. 3 shows a method of obtaining spectra by specular reflectance using a further alternative demonstrable end plate 41 and a modified probe 45. The end plate 41 carries an optical adaptation 42 which consists of two inclined reflecting surfaces arranged to give an angle of incidence of (say) 10° onto a sample 44 which is retained on the end of the probe 45 by means of a cylindrical end cap 43 so providing good thermal control of the temperature of the sample since that is again in close proximity to the heater 13 of the probe, while allowing an appropriate optical aperture for the sample. All other features are as described in relation to FIG. 1.

Figure 4:
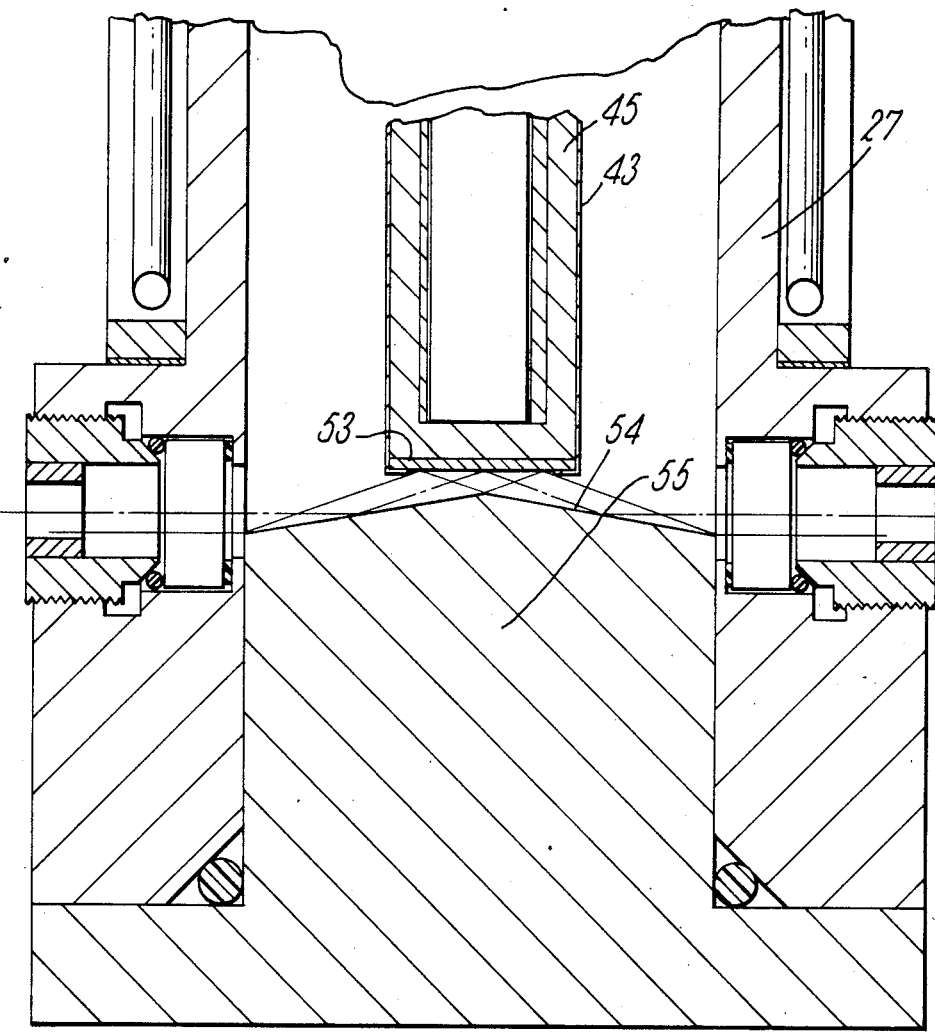

FIG. 4 shows another method of spectroscopy, Large Angle Reflectance, of particular importance in obtaining the infrared spectra of certain samples. A further modified demonstrable end plate 55 carries the optical adaptation this time consisting of two inclined reflecting surfaces 54 which provide an angle of incidence of (say) 70° to a sample 53. The sample is mounted on the end of the probe 45 and retained by a cylindrical sleeve 43 allowing an appropriate optical aperture for the sample. All other features are as described in relation to FIGS. 1 or 3 as appropriate.

What I claim is:

1. A cell for spectroscopy comprising:
   a housing having an outer surface, an inner surface and closure means;
   means in the housing for ingress and egress of radiation;
   a probe within the housing having first and second end portions;
   said first end portion being spaced from said inner surface and having means for mounting a sample to be spectroscopically examined by the radiation;
   means for controlling the temperature of the end of the probe; and
   means for controlling the temperature of the housing substantially independent of that of the probe.

2. A cell for spectroscopy comprising:
   a housing having an outer surface, inner surface and closure means;
   said inner surface of said housing progressively decreasing in diameter;
   means in the housing for ingress and egress of radiation;
   a probe within the housing having first and second end portions;
   said first end portion being spaced from said inner surface in the region of maximum diameter and having means for mounting a sample to be spectroscopically examined by the radiation; and
   means for controlling the temperature of the end of the prove substantially independent of the housing.

3. A cell for spectroscopy comprising:
   an housing having an outer surface, an inner surface and closure means;
   said inner surface progressively decreasing in diameter;
   means in the housing for ingress and egress of radiation;
   a probe within the housing having first and second end portions and having a wall thickness progressively decreasing in dimension from the first portion to the second portion;

said first end portion being spaced from the inner surface in the region of maximum dimension and having means for mounting a sample to be spectroscopically examined by the radiation; and means for controlling the temperature of the end of the probe substantially independent of that of the housing.

4. A cell for spectroscopy according to claim 1, wherein:

said second end portion of the probe is mounted to the housing by said closure means.

5. A cell for spectroscopy according to claim 1, wherein:

said first end portion of the probe having heating and/or refrigerating means associated therewith.

6. A cell for spectroscopy according to claim 1, wherein:

said first end portion having means for supporting a sample to be examined.

7. A cell for spectroscopy according to claim 6, wherein:

said support being arranged such that the portion of the sample impinged on by the radiation is most closely adjacent to the means for controlling the temperature of the end portion.

8. A cell for spectroscopy according to claim 7, wherein:

said support being arranged such that the examining radiation impinges on the sample off-center of the support.

9. A cell for spectroscopy according to claim 1, wherein:

said probe being hollow and being of substantially constant outer dimension.

10. A cell for spectroscopy according to claim 1, wherein:

said outer surface of said housing having temperature controlling means thereabout.

11. A cell for spectroscopy according to claim 10, wherein:

said temperature controlling means being tubes coiled around said outer surface and enclosed around the outer surface by jacket means.

12. A cell for spectroscopy according to claim 1, wherein:

said means for ingress and egress of radiation being removable windows.

13. A cell for spectroscopy according to claim 1, wherein:

said closure means being removal caps.

14. A cell for spectroscopy according to claim 13, wherein:

one of the said closures being in the region of maximum dimension of the inner surface.

15. A cell for spectroscopy according to claim 14, wherein:

said cap having optical surfaces allowing reflectance spectra of the sample to be obtained.

16. A cell for spectroscopy according to claim 1, wherein:

means within the housing for obtaining emission spectra from the sample.

17. A cell for spectroscopy according to claim 1, wherein:

said sample being subject to a maximum sustained temperature of at least 700° C. and a minimum sustained temperature of at least as low as $-170°$ C.

18. A cell for spectroscopy according to claim 1, wherein:

said sample being subject to a maximum pressure of at least 2000 psig or to a vacuum of better than 10 micro-torr while the sample is at elevated or low temperature.

19. A cell for spectroscopy according to claim 1, wherein:

said probe being metallic.

* * * * *